(12) United States Patent
Dahl et al.

(10) Patent No.: US 8,367,166 B2
(45) Date of Patent: Feb. 5, 2013

(54) SYNTHESIS OF HIGHER DIAMONDOIDS

(75) Inventors: Jeremy E. Dahl, Palo Alto, CA (US); J. Michael Moldowan, Sebastopol, CA (US); Michael A. Kelly, Portola Valley, CA (US); Robert M. Carlson, Petaluma, CA (US)

(73) Assignees: Chevron U.S.A. Inc., San Ramon, CA (US); The Board of Trustees of the Leland Stanford Junior University, Palo Alto, CA (US)

( * ) Notice: Subject to any disclaimer, the term of this patent is extended or adjusted under 35 U.S.C. 154(b) by 646 days.

(21) Appl. No.: 12/608,682

(22) Filed: Oct. 29, 2009

(65) Prior Publication Data

US 2010/0112214 A1    May 6, 2010

Related U.S. Application Data

(60) Provisional application No. 61/110,263, filed on Oct. 31, 2008.

(51) Int. Cl.
*C07C 13/28* (2006.01)
*C23C 16/00* (2006.01)

(52) U.S. Cl. ............ 427/577; 427/569; 585/352

(58) Field of Classification Search ............ None
See application file for complete search history.

(56) References Cited

U.S. PATENT DOCUMENTS

| | | | |
|---|---|---|---|
| 4,744,962 A * | 5/1988 | Johnson et al. | 423/235 |
| 6,743,290 B2 | 6/2004 | Dahl et al. | |
| 6,812,370 B2 | 11/2004 | Dahl et al. | |
| 6,812,371 B2 | 11/2004 | Dahl et al. | |
| 6,815,569 B1 | 11/2004 | Dahl et al. | |
| 6,828,469 B2 | 12/2004 | Dahl et al. | |
| 6,831,202 B2 | 12/2004 | Dahl et al. | |
| 6,843,851 B2 | 1/2005 | Dahl et al. | |
| 7,034,194 B2 | 4/2006 | Dahl et al. | |
| 7,094,937 B2 | 8/2006 | Dahl et al. | |
| 7,173,160 B2 | 2/2007 | Maesen et al. | |
| 2008/0191598 A1* | 8/2008 | Yang et al. | 313/310 |

OTHER PUBLICATIONS

Dahl, Angew. Chem. Int. Ed., V49, p. 9881, 2010.*
Dahl, Science, vol. 299, Jan, 2003, p. 96.*
Dahl, Nature, vol. 399, May, 1999, p. 54.*
Badziag, P. et al., "Nanometer-sized diamonds are more stable than graphite," *Nature* 343: 244-245 (1990).
Burns W. et al., "Gas-phase Reactions on Platinum. Synthesis and Crystal Structure of *anti*-Tetramantane, a Large Diamondoid Fragment," *J. Chem. Soc. Chem. Comm.*, 893-895 (1976).
Butler, J. and Woodin, R., "Chapter 2: Thin film diamond growth mechanisms," *Thin Film Diamond*, A. Lettington and J. W. Steeds, Eds., Chapman & Hall, London, pp. 15-30 (1994).
Carlson, R.M.K. et al., "Chapter 6: Diamond Molecules Found in Petroleum. New Members of the H-Terminated Diamond Series," *Proceedings of the NATO Advanced Research Workshop on Synthesis, Properties and Applications of Ultrananocrystalline Diamond*, St. Petersburg, Russia, Jun. 7-10, 2004, D.M. Gruen et al., Eds., Springer, The Netherlands, pp. 63-78 (2005).
Cupas, C. et at, "Congressane," *J. Am. Chem. Soc.* 87(4):917-918 (1965).
Decker H., *Zeitschrift für angewandte Chemie* 41:794-795 (1924).

(Continued)

*Primary Examiner* — Joseph Miller, Jr.
(74) *Attorney, Agent, or Firm* — Merchant & Gould

(57) ABSTRACT

In some embodiments, the present invention is directed to methods for synthesizing higher diamondoids, wherein said methods involve augmenting existing diamondoid molecules through the bonding of carbon atoms to such existing diamondoid species with intramolecular cross-linking so as to form larger diamondoids containing face-fused diamond-crystal (adamantane) cages with carbon frameworks superimposable on the cubic-diamond crystal lattice.

18 Claims, 7 Drawing Sheets

[1(2)3]      [121]      [123]P      [123]M

OTHER PUBLICATIONS

Gund, T.M. et al, "Computer Assisted Graph Theoretical Analysis of Complex Mechanistic Problems in Polycyclic Hydrocarbons. The Mechanism of Diamantane Formation from Various Pentacyclotetradecanes," *J. Am. Chem. Soc.* 97(4):743-751 (1975).

Hollowood and McKervey, "Synthesis of Triamantane," *J. Org. Chem.* 45(24):4954-4958 (1980).

Kirchen R.P. et al., "A mechanistic study of the carbocation route from tetrahydrodicyclopentadiene to the adamantane ring," *Can. J Chem.* 71:2016-2027 (1993).

McKervey M.A., "Synthetic Approaches to Large Diamondoid Hydrocarbons," *Tetrahedron* 36: 971-992 (1980).

Osawa, E. et al., "The Mechanism of Carbonium Ion Rearrangements of Tricycloundecanes Elucidated by Empirical Force Field Calculations," *J Am. Chem. Soc.* 99(16):5361-5373 (1977).

Osawa, E. et al., "Thermodynamic Rearrangements of Larger Polycyclic Hydrocarbons Derived from the 38.5 and 41.5° C Melting Dimers of Cyclooctatetraene. Crystal and Molecular Structures of 5-Bromoheptacyclo[$8.6.0.0^{2,8}.0^{3,13}.0^{4,11}.0^{5,9}.0^{12,16}$] hexadecane (5-Bromo-($C_2$)-bisethanobisnordiamantane), 6,12-Dibromoheptacyclo[$7.7.0.0^{2,6}.0^{3,15}.0^{4,12}.0^{5,10}.0^{11,16}$] hexadecane, and Nanocyclo [$11.7.1.1^{2,18}.0^{3,16}.0^{4,13}.0^{5,10}.0^{6,14}.0^{7,11}.0^{15,20}$]docosane (Bastardane)[1,2]," *J Org. Chem.* 45(15):2985-2995 (1980).

Prelog S., "Synthesis of adamantine," *Vierundsiebzigster Jahrgang* 74:1644-1648 (1941).

Schleyer, P.v.R., "A simple preparation of adamantine," *J Am. Chem. Soc.* 79: 3292 (1957).

Whitlock, Jr., H. and Siefken, M., The Tricyclo[$4.4.0.0^{3,8}$]decane to Adamantane Rearrangement, *J. Am. Chem. Soc.* 90(18): 4929-4939 (1968).

Williams, Jr. V. Z. et al., "Triamantane," *J. Am. Chem. Soc.* 88(16): 3862-3863 (1966).

Winter, N. and Ree, F., Carbon particle phase stability as a function of size, *J. Computer-Aided Materials Design* 5:279-294 (1998).

\* cited by examiner

SYNTHESIS OF HIGHER DIAMONDOIDS

This application claims priority to U.S. Provisional Patent Application No. 61/110,263, filed Oct. 31, 2008, the contents of which are incorporated herein by reference in their entirety.

FIELD OF THE INVENTION

1. Background of the Invention

The present invention relates to a process for synthesizing higher diamondoids. More specifically, the process involves augmenting diamondoid molecules through the bonding of carbon atoms to smaller diamondoid species with intramolecular cross-linking to form larger diamondoids containing face-fused diamond-crystal (adamantane) cages with carbon frameworks superimposable on the cubic-diamond crystal lattice.

2. Description of Related Art

Although the structure of a molecule containing a cubic diamond crystal cage was first proposed by Decker in 1924, its synthesis proved extraordinarily difficult. The first successful synthesis of "adamantane" (the smallest diamondoid, containing only a single diamond crystal cage) was not achieved until 1941, and then with a yield of only 0.16%. In 1957, Schleyer discovered that adamantane can be formed in high yields from $C_{10}$ tricyclic intermediates by carbocation-mediated thermodynamically-controlled equilibration reactions. He used this method to also synthesize diamantane (a diamondoid containing two diamond crystal cages). An alternative name for diamantane is "congressane" because its synthesis had been posed as an exceedingly difficult challenge to chemists at the Nineteenth Congress of the International Union of Pure and Applied Chemistry.

The overall reaction of a strained $C_{14}H_{20}$ polycyclic isomer, e.g., tetrahydrobisnor-S, to yield diamantane by the carbocation-mediated equilibration is in fact a staggeringly complex network of thousands of reaction pathways. Graphical analysis of the mechanisms for adamantane formation from endo-tetrahydrodicyclopentadiene shows an amazing 2897 different pathways (Whitlock, et al., 1968), many of the details of which have now been verified. Graphical analyses have also been performed for carbocation equilibration reactions leading to the diamondoids methyladamantane and diamantane. Limited analysis of the heptacyclooctadecane (triamantane) system suggests the existence of at least 300,000 intermediates.

The synthesis of triamantane by carbocation-mediated thermodynamically-controlled equilibration reactions was achieved in 1966. Since then, exhaustive research has established that higher diamondoids (diamondoids containing more than three face-fused diamond crystal cages) cannot be synthesized by the superacid-carbocation equilibration methods. Accordingly, a characteristic that distinguishes the lower diamondoids from the higher ones is that lower diamondoids can be synthesized by carbocation equilibration reactions while higher diamondoids can not. In fact only one of the higher diamondoids, [121]tetramantane, has ever been synthesized, and this by a complex, low-yielding, gas-phase double homologation of diamantane (Burns et al., *J. Chem. Soc., Chem. Commun.*, 1976, pp. 893).

In 1980, the likelihood of the development of successful higher diamondoid syntheses was assessed and it was concluded that prospects were extremely unlikely because of a lack of large polycyclic precursors, increasing problems with rearranging intermediates becoming trapped in local energy minima, rising potential for disproportionation reactions leading to unwanted side products, and rapidly expanding numbers of isomers as carbon numbers of target higher diamondoid products increase (Osawa et al., 1980). With the failure to implement carbocation-mediated syntheses of higher diamondoids, attempts to synthesize higher diamondoids were largely abandoned in the 1980's.

Although attempts to synthesize higher diamondoids have up to now been unsuccessful, the thermodynamic stabilities of higher diamondoids are high relative to other hydrogenated carbon materials of comparable nanometer size.

Attempts to identify the presence of higher diamondoids in diamond products formed by a $CO_2$-laser-induced gas-phase synthetic methods and diamond materials produced by commercial chemical vapor disposition (CVD) using methane as the carbon source have been unsuccessful. Unlike the synthetic chemical approaches discussed above which employ carbocation reaction mechanisms, these gas-phase diamond-forming processes involve free-radical reaction mechanisms (Butler et al., *Thin Film Diamondoid Growth Mechanisms in Their Film Diamondoid*, Lettington and Steeds Eds., London, Chapman & Hall, pp. 15-30, 1994). Thus, it previously appeared that no method for synthesizing higher diamondoids would be found.

Although they have never been synthesized, the existence of higher diamondoids in petroleum and their isolation for commercial applications has now been successful. However, a process for successfully synthesizing higher diamondoids would be of great value to the industry.

SUMMARY OF THE INVENTION

In some embodiments of the present invention, there is provided a method (or methods) for synthesizing higher diamondoid molecules. The method comprises sufficiently heating (or otherwise activating) diamondoid molecules having at least three cages so as to break carbon-carbon bonds to form small reactive carbon species, and then allowing a reaction to occur between these reactive species and diamondoid molecules having at least three cages to thereby add sufficient carbon atoms (that cross-link with dehydrogenation) to add at least one diamond crystal (adamantane) cage to such diamondoid molecules. The synthesized higher diamondoid molecules are then recovered. The heating can take place in a closed reactor, generally under an inert atmosphere, or the heating can take place in a chemical vapor deposition (CVD)-type chamber using a filament (or other excitation source) to create a concentration of reactive carbon species. Certain nondiamondoid carbon species, for example norbornane, isobutene, isobutane, can be added to the reaction mixture to promote the reaction, generating larger yields of higher diamondoids. Synthesized higher diamondoid molecules made via methods of the present invention are herein often referred to as "augmented higher diamondoids" or "synthetic higher diamondoids" (the terms are synonymous) to distinguish them from naturally-occurring higher diamondoids.

Among other factors and mechanisms, the present invention has discovered that higher diamondoids can be synthesized by employing free-radical reaction pathways. The reaction generally involves the addition of four carbons to a diamond face, controlled by steric effects such as those involving 1-3 diaxial interactions, thereby resulting in the formation of a new diamond crystal cage and the next larger diamondoid in the series (of progressively larger diamondoids). Particularly effective is the use of a gas phase reaction using the kinds of free radical reactions responsible for the growth of CVD-diamond. Smaller diamondoids act as seeds from which the next larger diamondoids are grown. Surface hydrogen atoms are removed and replaced by carbon-containing radicals generated from diamondoid starting material or certain added reactants, such as norborane. The process provides a method by which an effective synthesis of valuable nanomaterials (e.g., the higher diamondoids) can be achieved.

DETAILED DESCRIPTION OF THE PREFERRED EMBODIMENTS

Figure 1:
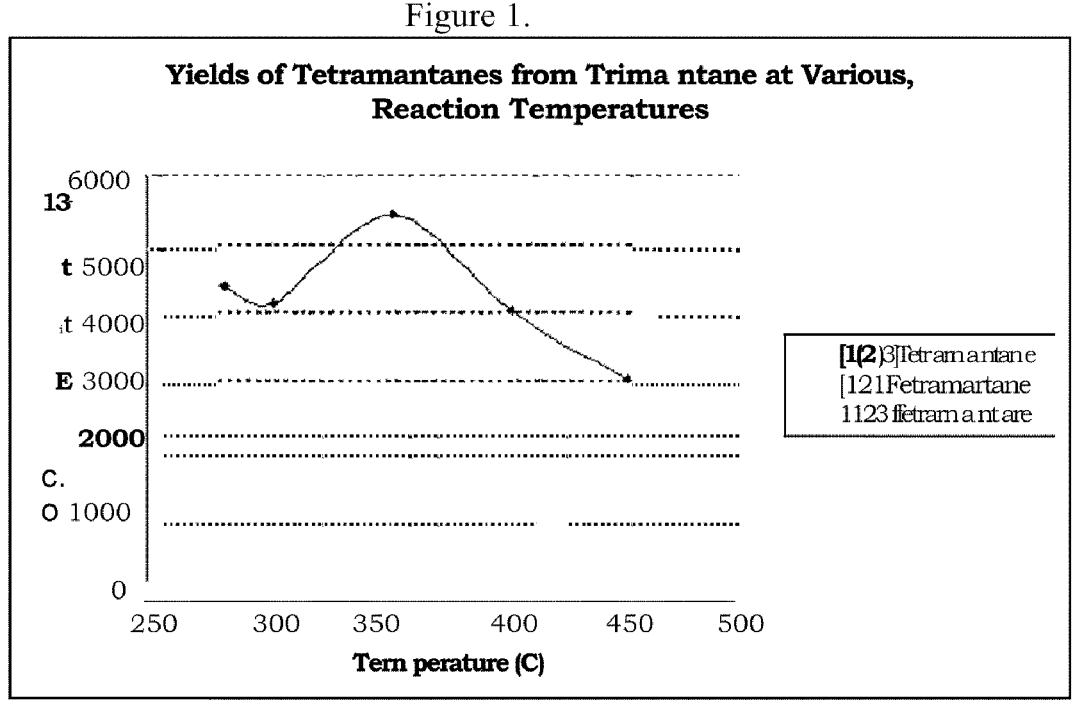
FIG. 1 illustrates changing yields of tetramantane higher diamondoids from triamantane with changing reaction temperatures.
Figure 2:
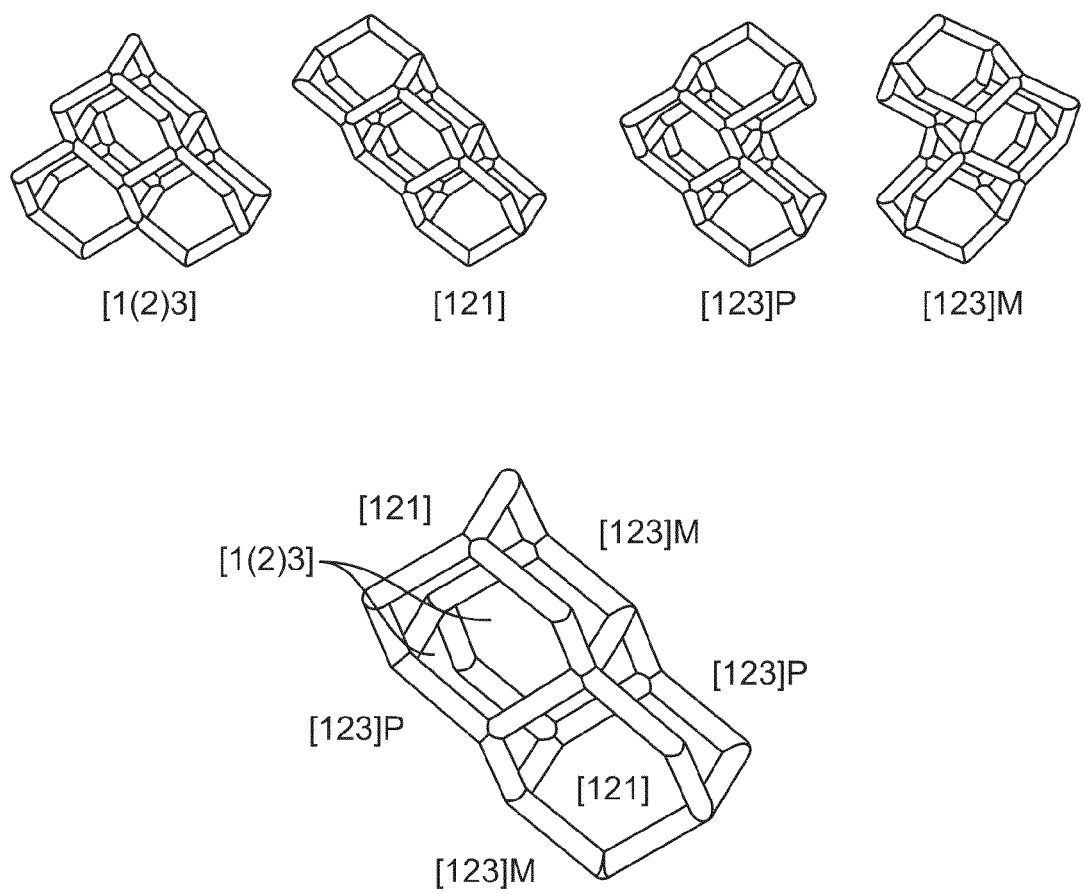
FIG. 2 illustrates the carbon framework structures of the four possible tetramantane higher diamondoids and where each is grown from specific faces of the triamantane starting molecules.

Higher diamondoids are nanometer-sized diamond molecules (containing 4 or more face-fused diamond crystal cages) having properties, such as negative-electron-affinity, that are valuable for commercial application in the microelectronics and other industries. Unlike the lower diamondoids (i.e., adamantane, diamantane and triamantane), higher diamondoids e.g., as discussed in U.S. Pat. Nos. 6,815,569; 6,843,851 ; 7,094,937; 6,812,370; 6,828,469; 6,831,202; 6,812,371; 7,034,194; 6,743,290, which are hereby incorporated by reference in their entirety, with the exception of one of the tetramantanes, have never been synthesized, despite intensive efforts to do so.

The present invention provides an effective and efficient method for synthesizing higher diamondoids. More specifically, it has been discovered that tetramantanes can be made from triamantane, that pentamantanes can be made from tetramantanes, and so on. In accordance with some embodiments of the present invention, the method involves the heating of diamondoid species (material) having at least three cages in a reactor. The reaction temperature is typically in the range of from 200-600° C. The reaction can be done with or without a catalyst, and is typically carried out under an inert atmosphere (at least initially). With a catalyst, reaction temperatures can be lower, e.g., preferably 275-475° C., more preferably 300-400° C., and most preferably 325-375° C. Without a catalyst, a higher temperature is employed, preferably in the range of 400-600° C., and more preferably in the range of 450-550° C.

Higher diamondoids can also be formed via gas-phase reactions employing the kinds of free-radical reactions responsible for the growth of CVD-diamond. In such processes, smaller diamondoids act as seeds from which the next larger diamondoids are grown. In such processes, surface hydrogen atoms are removed and replaced by carbon-containing radicals generated from diamondoid starting material and/or certain added reactants, such as isobutane. Four-carbon additions to a diamond face, at 1-3 diaxial sites formed via hydrogen abstractions, result in the formation of a new diamond crystal cage and the next larger diamondoid in the series.

Those of skill in the art will recognize that numerous variations exist on the above-described methods of the present invention, and that these variations are seen to fall within the scope of the instant invention, especially wherein they provide for augmented or synthetically-derived higher diamondoid species. Examples of such variations include, but are not limited to, reactant precursor composition and activation means (e.g., thermal, photolytic, and/or chemical) for providing reactant species.

In the examples below, diamondoid material is heated in a sealed, evacuated 316 stainless steel reaction vessel, and the presence and absence of a clay mineral (montmorillonite), with and without additional hydrocarbon reactants. A variety of reaction times and temperatures were employed and studied. After a given reaction was complete, the products were extracted and analyzed. Reaction products include alkylated forms of the starting diamondoid, smaller diamondoids, and valuable larger diamondoids. These examples are provided to demonstrate particular embodiments of the present invention. It should be appreciated by those of skill in the art that the methods disclosed in the examples which follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLE 1

The first reactant was the lower diamondoid triamantane ($C_{18}H_{24}$), isolated from petroleum and recrystallized 8-times to remove higher diamondoids. See, e.g., U.S. Pat. No. 7,173, 160 for isolation of diamondoids from petroleum. Diamondoid impurities remaining in the starting materials after recrystallization were determined quantitatively by gas chromatography-mass spectrometry (GCMS) and referenced to the starting weight of triamantane reactant. [121]tetramantane, at a concentration of 10.5 ppm, was the only higher diamondoid detected in the recrystallized triamantane. The triamantane was loaded into the 316 stainless steel reaction vessel and montmorrilonite clay was added. The results of one series of reactions are shown in Table 1. This reaction series used identical conditions, except that a different hydrocarbon reactant was added to each reaction mixture. However, one experiment used triamantane without added hydrocarbons, i.e., neat. The objective was to study the possible reaction of triamantane with other compounds and with itself

TABLE 1

Yields of Individual Tetramantane Products from Triamantane Alone and
with Various Added Reactants in the Presence of Montmorillonite Catalyst
for 96 at 280° C.

| | Reactants | | | | |
|---|---|---|---|---|---|
| Products | Triamantane neat | Triamantane & Adamantane | Triamantane & Diamantane | Triamantane & Norbornane | Triamantane & Norbornane |
| [1(2)3]Tetramantane | 2433 | 731 | 539 | 4365 | 4377 |
| [121]Tetramantane | 1176 | 407 | 318 | 1692 | 1333 |
| [123]Tetramantane | 880 | 32 | 30 | 201 | 123 |

(Yields are given as ppm of starting triamantane. 25 mg of triamantane and 25 mg of montmorillonite were used in each experiment).

Surprisingly, results listed in Table 1 show that most of the additional reactants inhibit rather than promote tetramantane formation. Triamantane alone generated tetramantane products, but yields dropped when adamantane or diamantane was added to the reaction mixture. Similar tetramantane product inhibition was found when hexane, 1,4-dimethylcyclohexane, bi-adamantane, bicylcoheptadiene, decaline or cubane was added. Only norborane improved yields of [1(2)3]tetramantane (by a factor of 1.8). However, yields of the other two tetramantanes fell relative to yields using only triamantane as the starting material.

TABLE 2

Yields of Individual Tetramantane Products from Triamantane
and Norborane Reactants in the Presence of Montmorillonite
Catalyst for 96 Hours at Various Temperature

| Product | 280° C. | 280° C. | 300° C. | 350° C. | 400° C. | 450° C. |
|---|---|---|---|---|---|---|
| [1(2)3]Tetramantane | 4365 | 4377 | 4132 | 5403 | 4026 | 2993 |
| [121]Tetramantane | 1692 | 1333 | 1640 | 2111 | 1379 | 401 |
| [123]Tetramantane | 201 | 123 | 211 | 173 | 72 | 9 |

(Yields are given as ppm of starting triamantane. 25 mg of triamantane, montmorillonite, and norborane were used in each experiment).

Table 2 lists results for a series of experiments, each run for 96 hours but at varying temperatures, the temperatures ranging from 280° C. up to 450° C. FIG. 1 is a plot of the data from Table 1 showing the yields of the three tetramantanes as a function of reaction temperature. A reaction temperature of approximately 350° C. gave the highest yields of tetramantanes under these conditions. The main products of the reactions are alkylated triamantanes. While not intending to be bound by theory, it is presumed that some of the triamantane in the reaction mixture cracks, thereby forming hydrocarbon radicals that can abstract hydrogen from intact triamantanes, forming stable alkyltriamantanes products. In addition to alkylated triamantanes, all three of the tetramantane higher diamondoids are formed.

EXAMPLE 2

In addition to triamantane, the three structural forms of tetramantane were also isolated and reactions were conducted with them to determine if any of the 6 stable, molecular weight (mw) 344, pentamantanes could be synthesized. Pentamantanes that are formed by the replacement of 3 tetramantane tri-axial hydrogens with a 4-carbon isobutane-shaped unit to form a new closed cage without breaking any of the original tetramantane carbon-carbon bonds—are highly favored. The most favored of these are those with the least steric hindrance associated with access to the tetramantane reactant face.

Figure 3:
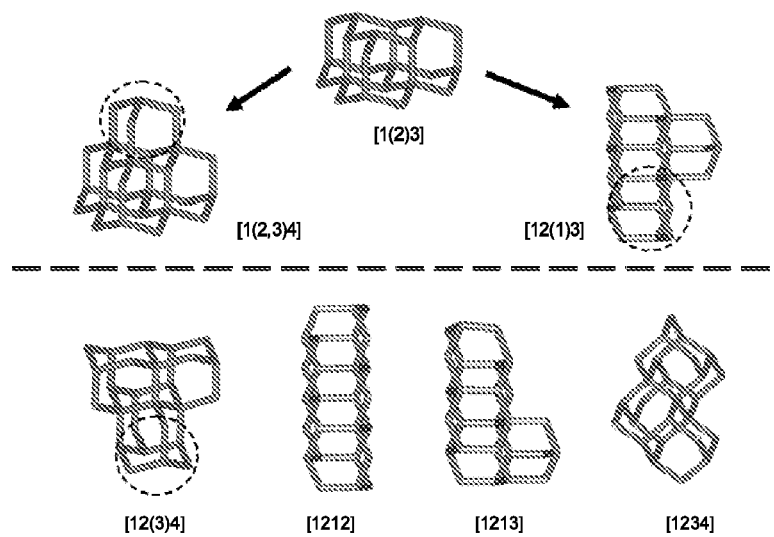
FIG. 3 illustrates the carbon framework structures of pentamantane higher diamondoids and which can be grown from [1(2)3]tetramantane.

Table 3 presents results of experiments using [1(2)3]tetramantane as a starting material. The only possible pentamantanes that can be derived from the addition of 4 carbons to this tetramantane are [1(2,3)4]pentamantane, [12(1)3]pentamantane, and [12(3)4]pentamantane (FIG. 3). In Table 3 it can be seen that two of these three pentamantanes were synthesized by the process. FIG. 3 illustrates the carbon frame-work structures of the six pentamantane higher diamondoids and indicates which can be grown from [1(2)3]tetramantane. Diamond crystal cages that can be added to [1(2)3]tetramantane are circled with dashed lines. Structures above the straight, horizontal dashed line in FIG. 3 are found in the reaction products, while structures below the line are not found, or found at trace levels. As measure of steric interference, Table 3 lists the number of 1,3-diaxial interactions associated with reactant faces from which specific pentamantanes could be formed by direct face-fusing of a diamond cage to [1(2)3] tetramantane. The data show that steric effects control which pentamantanes are formed from [1(2)3]tetramantane. Also shown in Table 3 are the number of ways in which a four carbon addition to a particular tetramantane will result in a particular pentamantane. This seems to be much less important than steric considerations.

TABLE 3

Production of Pentamantane Products from [1(2)3]Tetramantane 280°
C., Montmorillonite Catalyst, Reaction time = 96 hours

| | Pentamantane Yields and Characteristics | | |
|---|---|---|---|
| Specific Pentamantane Products | Specific Pentamantane Products (ppm) | Number of 1,3-Diaxial Interactions on Tetramantane Reactant Face | Number of Tetramantane Reactant Faces That Can Form Specific Pentamantane |
| [1(2,3)4]Pentamantane | 7030 | 3 | 1 |
| [12(1)3]Pentamantane | 1417 | 6 | 6 |
| [1212]Pentamantane | | | |

TABLE 3-continued

Production of Pentamantane Products from [1(2)3]Tetramantane 280° C., Montmorillonite Catalyst, Reaction time = 96 hours

| | Pentamantane Yields and Characteristics | | |
|---|---|---|---|
| Specific Pentamantane Products | Specific Pentamantane Products (ppm) | Number of 1,3-Diaxial Interactions on Tetramantane Reactant Face | Number of Tetramantane Reactant Faces That Can Form Specific Pentamantane |
| [1213]Pentamantane | | | |
| [12(3)4]Pentamantane | | 12 | 3 |
| [1234]Pentamantane | | | |

(Yields are given as ppm of starting material, [1(2)3]tetramantane. 9.0 mg of [1(2)3]tetramantane was used as starting material)

Even in this un-optimized reaction, the yield of valuable pyramidal [1(2,3)4]pentamantane is approaching 1 weight percent.

Table 4 presents results of experiments using [121]tetramantane as a starting material. In Table 4 it is seen that three of the six mw 344 pentamantanes were synthesized by the process.

TABLE 4

Production of Pentamantane Products from [121]Tetramantane 280° C., Montmorillonite Catalyst, Reaction time = 96 hours

| | Pentamantane Yields and Characteristics | | |
|---|---|---|---|
| Specific Pentamantane Products | Specific Pentamantane Products (ppm) | Number of 1,3-Diaxal Interactions on Tetramantane Reactant Face | Number of Tetramantane Reactant Faces That Can Form Specific Pentamantane |
| [1(2,3)4]Pentamantane | | | |
| [12(1)3]Pentamantane | 655 | 6 | 4 |
| [1212]Pentamantane | 2965 | 3 | 2 |
| [1213]Pentamantane | 332 | 6 | 4 |
| [12(3)4]Pentamantane | | | |
| [1234]Pentamantane | | | |

(Yields are given as ppm of starting material, [121]tetramantane. 10.8 mg of [121]tetramantane was used as starting material)

Figure 4:
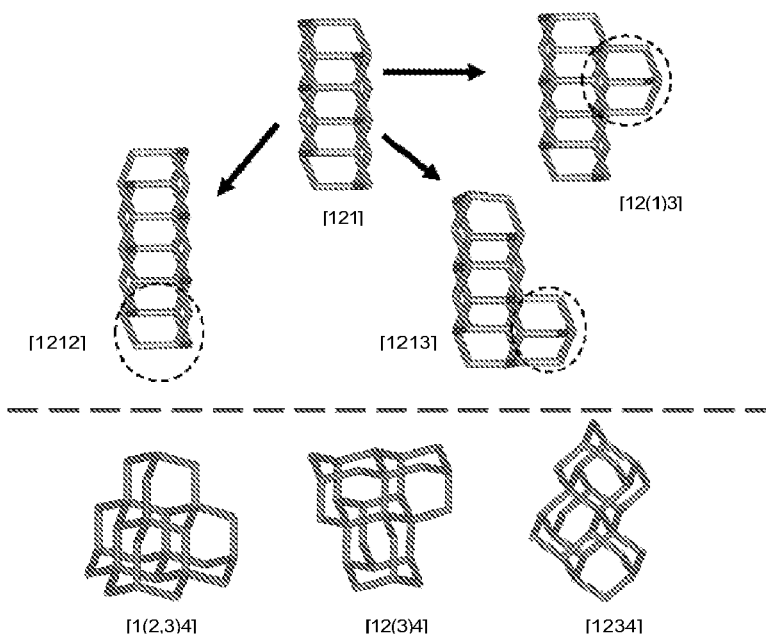
FIG. 4 illustrates the carbon framework structures of pentamantane higher diamondoids and which can be grown from [121]tetramantane.

As measure of steric interference, Table 4 lists the number of 1,3-diaxial interactions associated with reactant faces from which specific pentamantanes could be formed by direct face-fusing of a diamond cage to [121]tetramantane. FIG. 4 illustrates the carbon frame-work structures of the six pentamantane higher diamondoids and indicates which of these can be grown from [121]tetramantane. Diamond crystal cages that can be added to [121]tetramantane are circled with dashed lines. Structures above the straight, horizontal dashed line in FIG. 4 are found in the reaction products, while structures below the line are not found, or found at only trace levels. Again, the data show that steric effects control which pentamantanes are formed from [121]tetramantane, whereas the number of ways a specific pentamantane could be formed (Table 4) is not important. Even in this un-optimized reaction, the yield of valuable rod-shaped [1212]pentamantane is already ca. 0.3 weight percent.

TABLE 5

Production of Pentamantane Products from [123]Tetramantane 280° C., Montmorillonite Catalyst, Reaction time = 96 hours

| | Pentamantane Yields and Characteristics | | |
|---|---|---|---|
| Specific Pentamantane Products | Specific Pentamantane Products (ppm) | Number of 1,3-Diaxial Interactions on Tetramantane Reactant Face | Number of Tetramantane Reactant Faces That Can Form Specific Pentamantane |
| [1(2,3)4]Pentamantane | | | |
| [12(1)3]Pentamantane | 5971 | 3 | 2 |
| [1212]Pentamantane | | | |
| [1213]Pentamantane | 1403 | 3 | 2 |
| [12(3)4]Pentamantane | | 5 | 2 |
| [1234]Pentamantane | | 5 | 2 |

(Yields are given as ppm of starting material, [123]Tetramantane. 13.1 mg of [123]tetramantane was used as starting material)

Figure 5:
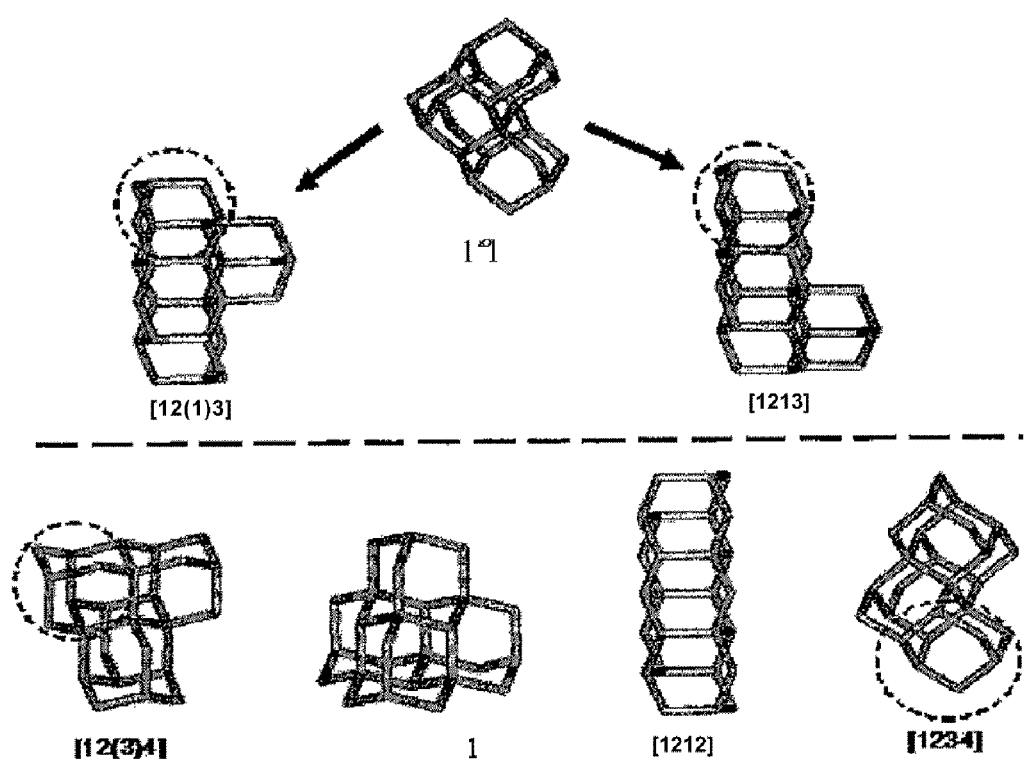
FIG. 5 illustrates the carbon framework structures of pentamantane higher diamondoids and which can be grown from [123]tetramantane.

Table 5 presents results of experiments using [123]tetramantane as a starting material. In Table 5 it is seen that two of the mw 344 pentamantanes were synthesized by the process. As measure of steric interference, Table 5 lists the number of 1,3-diaxial interactions associated with reactant faces from which specific pentamantanes could be formed by direct face-fusing of a diamond cage to [123]tetramantane. FIG. 5 illustrates the carbon frame-work structures of the six pentamantane higher diamondoids and indicates which can be grown from [123]tetramantane. Diamond crystal cages that can be added to [123]tetramantane are circled with dashed lines. Structures above the straight, horizontal dashed line in FIG. 5 are found in the reaction products, while structures below the line are not found, or found at trace levels. Again, the data show that steric effects control which pentamantanes are formed from [123]tetramantane, whereas the number of ways a specific pentamantane could be formed (Table 5) is not important. Even in this un-optimized reaction, the yield of valuable [12(1)3]pentamantane is already ca. 0.6 weight percent.

As stated previously, the pentamantanes that form experimentally from a particular tetramantane are the pentamantanes that can be formed by the addition of 4 carbons. Where the breaking of a tetramantane cage is required to form a particular pentamantane, that pentamantane will either not be generated from that particular tetramantane or it will be in very small relative amounts. The 4 carbons that are added take the form of isobutane and replace 3 tri-axial hydrogens on the tetramantane surface.

Starting with the linear [121]tetramantane, one can create a cage at the end of the molecule, extending the linear arrangement, to give the [1212]pentamantane. Alternatively, one could create a cage on the side of [121]tetramantane, which would give either [12(1)3] or [1213]pentamantane. One could not, however, form either [1(2,3)4], [12(3)4], or [1234] pentamantane without breaking cages and reconstructing the molecule. Interestingly, it is clear from Table 4 that the main products of reacting [121]tetramantane are [1212], [12(1)3] and [1213]pentamantane. Addition of the extra cage at one of the ends would involve the least steric hindrance, and this addition at the ends seems to be born out experimentally by the favored formation of [1212]pentamantane.

For [1(2)3]tetramantane, it is possible to put the isobutyl group on the top to form the pyramidal [1(2,3)4]pentamantane. Additionally, by completing cages along the sides of this tetramantane one can make [12(1)3] or [12(3)4]pentamantane. Table 3 shows that the predominant pentamantanes made by experimental pyrolysis of [1(2)3]tetramantane are in fact [1(2,3)4] or [12(1)3]pentamantane. Addition of the new cage to form [1(2,3)4]pentamantane would have the least steric hindrance and indeed [1(2,3)4]pentamantane is the predominant product. No [12(3)4]pentamantane was detected from the experiment and there was a slight amount of [1212] pentamantane, the latter of which would have had to have been formed by another mechanism.

Lastly, by adding an isobutyl to [123]tetramantane, one could theoretically make [1234], [12(3)4], [1213] and [12(1)3]pentamantane. Steric considerations would favor the formation of [12(1)3]pentamantane. Experimental data in Table 5 show that all of these pentamantanes are in fact formed, with [12(1)3]pentamantane predominating. No detectable [1(2,3)4]pentamantane was formed, and only trace amounts of [1212]pentamantane were seen, presumably formed by a different mechanism.

EXAMPLE 3

A series of experiments were performed to determine the importance of the montmorillonite clay in the synthesis of the higher diamondoids. Triamantane was sealed in an inert gold tube without montmorillonite catalyst and heated to 500° C. for 96 hours. Even without the montmorillonite the formation of higher diamondoids, both tetramantanes and pentamantanes was observed, as shown in Table 6. The reaction temperatures needed to be increased compared to the temperatures for reactions in the presence of montmorillonite, but yields were comparable. This result demonstrates that the montmorillonite is not essential for the higher diamondoid formation reaction.

TABLE 6

Production of Tetramantane and Pentamantane Products from Triamantane without Catalyst at 500° C., and with Isobutane or Isobutene (at 500° C. without Catalyst)

|  | Triamantane, neat | Triamantane & Isobutane | Triamantane & Isobutene |
|---|---|---|---|
| [1(2)3]Tetramantane | 1567 | 11413 | 16274 |
| [121]Tetramantane | 718 | 7163 | 8576 |
| [123]Tetramantane | 183 | 1304 | 1782 |
| [1(2,3)4]Pentamantane | 2 | 183 | 141 |
| [12(1)3]Pentamantane | 13 | 299 | 229 |
| [1212]Pentamantane | 5 | 182 | 137 |
| [1213]Pentamantane | 6 | 125 | 92 |
| [12(3)4]Pentamantane | 0.9 | 8 | 9 |
| [1234]Pentamantane | 0.4 |  |  |

Reaction time = 96 hours. Yields are given as ppm of starting material, triamanatane. Reactants were sealed in evacuated gold tubes.

Because each diamondoid cage closure requires four carbons in an isobutyl configuration, isobutane and isobutene were added to the reaction as carbon sources for the additional higher diamondoid cages. Table 6 shows that yields of higher diamondoids can be greatly increased by the addition of either isobutene or isobutane to the reaction mixture.

TABLE 7

Production of pentamantane products from [121]tetramantane

| | Reactants | | |
|---|---|---|---|
| Products | [121]Tetramantane (ppm) | [121]Tetramantane & Isobutane (ppm) | [121]Tetramantane & Isobutene (ppm) |
| [1(2,3)4]Pentamantane |  |  |  |
| [12(1)3]Pentamantane | 104 | 2922 | 1005 |
| [1212]Pentamantane | 114 | 7637 | 1970 |
| [1213]Pentamantane | 34 | 2634 | 617 |
| [12(3)4]Pentamantane |  |  |  |
| [1234]Pentamantane |  |  |  |

* Neat with isobutane or isobutene at 500° C. under argon in sealed gold tube
^ Neat at 500° C. under argon in sealed gold tube

TABLE 8

Production of pentamantane products from [1(2)3]tetramantane

| | Reactants | | |
|---|---|---|---|
| Products | [1(2)3]Tetramantane (ppm) | [1(2)3]Tetramantane & Isobutane (ppm) | [1(2)3]Tetramantane & Isobutene (ppm) |
| [1(2,3)4]Pentamantane | 1723 | 2995 | 1341 |
| [12(1)3]Pentamantane | 332 | 2552 | 872 |
| [1212]Pentamantane |  | 62 | 21 |
| [1213]Pentamantane |  | 79 | 6 |
| [12(3)4]Pentamantane |  | 62 | 11 |
| [1234]Pentamantane |  |  |  |

* Neat with isobutane or isobutene at 500° C. under argon in sealed gold tube
^ Neat at 500° C. under argon in sealed gold tube

TABLE 9

Production of pentamantane products from [123]tetramantane

| Products | Reactants | | |
|---|---|---|---|
| | [123]Tetramantane (ppm) | [123]Tetramantane & Isobutane (ppm) | [123]Tetramantane & Isobutene (ppm) |
| [1(2,3)4]Pentamantane | | | |
| [12(1)3]Pentamantane | 497 | 5886 | 1116 |
| [1212]Pentamantane | 214 | 231 | 37 |
| [1213]Pentamantane | 41 | 3318 | 613 |
| [12(3)4]Pentamantane | 39 | 462 | 60 |
| [1234]Pentamantane | | 638 | 97 |

\* Neat with isobutane or isobutene at 500° C. under argon in sealed gold tube

^ Neat at 500° C. under argon in sealed gold tube

Similar runs, without any catalyst, where run to test conversion of individual tetramantane higher diamondoids into pentamantane higher diamondoids. Table 7 shows results using neat [121]tetramantane neat, with isobutene or isobutene, sealed in a gold tube under argon atmosphere and heated to 500° C. for 96 hours. Table 8 shows results using neat [1(2)3]tetramantane neat, with isobutene or isobutene, sealed in a gold tube under argon atmosphere and heated to 500° C. for 96 hours. Table 9 shows results using neat [123]tetramantane neat, with isobutene or isobutene, sealed in a gold tube under argon atmosphere and heated to 500° C. for 96 hours. These results further demonstrate that the montmorillonite is not essential for the higher diamondoid formation reaction and that yields of higher diamondoids can be greatly increased by the addition of either isobutene or isobutane to the reaction mixture.

It is clear from the experiments above (Examples 1-3) that diamondoids are being "built up" by the addition of carbons, some replacing hydrogens to complete a cage or cages and form larger diamondoids. This mechanism is analogous to the growth of chemical vapor deposition (CVD) diamond. CVD diamond is typically grown in a very reducing hydrogen atmosphere (typically over 90%), much of it in atomic form to keep carbon-carbon double bonds from forming. Diamond growth is derived from the addition of methyl and/or ethyl radicals replacing hydrogen on the surface of small diamond seeds which are necessary for initiation of the process. In this way, new cages are formed and the size of the diamond increased. This process takes place at fairly high temperatures, generally in excess of 450° C.; however, pressures are low, usually near atmospheric. Conditions are much less optimal for higher diamondoid growth in natural gas fields, but the time frames are considerable, with oil generation and oil cracking taking place on the order of millions of years or more. This leads to the conclusion that if conditions were optimal, i.e., conditions used to grow CVD diamond, that it would be possible to effectively synthesize higher diamondoids and larger nanodiamondoids of a particular size range using lower diamondoids as seeds.

Figure 6:
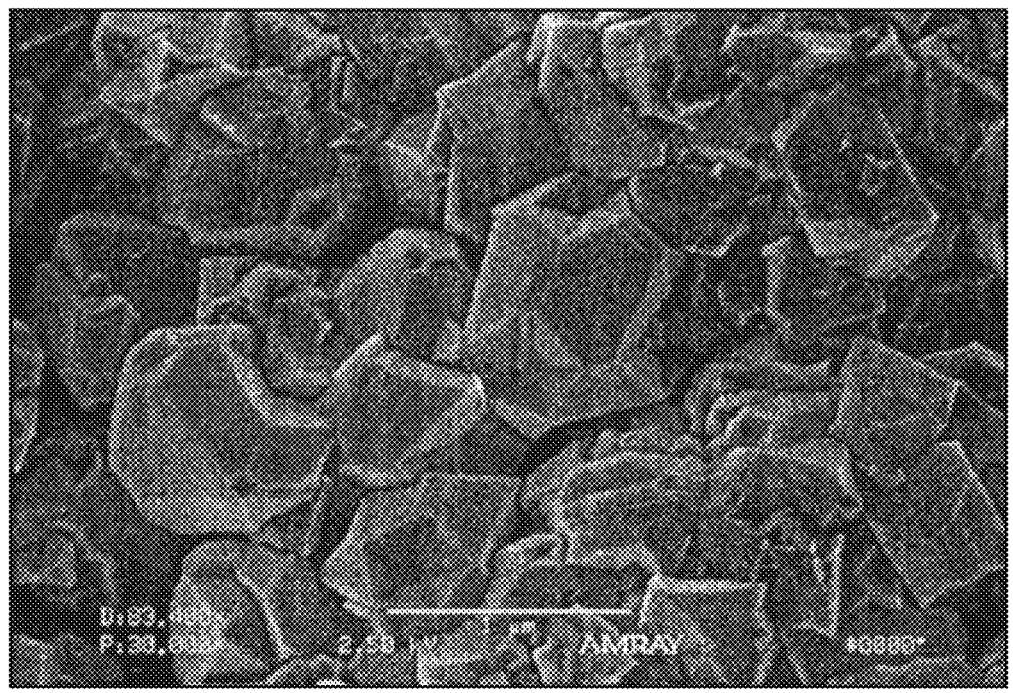
FIG. 6 is a scanning electron micrograph (SEM) of diamond produced by chemical vapor deposition (CVD) nucleated by higher diamondoids.

FIG. 6 is a scanning electron micrograph (SEM) of diamond produced by chemical vapor deposition (CVD) nucleated using alkyltetramantane higher diamondoids. This shows that diamondoids like the tetramantanes can act as seeds from which larger diamond crystals can be grown. The key is to identify conditions that stop the growth of the crystals growing from the diamondoid seed while particle sizes are still in the 1 to 2 nanometer size range.

These experimental conditions are less than ideal for growing CVD diamond (they were designed to mimic petroleum formation and oil cracking), yet they generated higher diamondoids with a yield of about 1%. Based on these results, if conditions are optimized in the CVD chamber small diamondoids seeds will readily grow larger diamondoids in the vapor phase. One could start with adamantane, diamantane or triamantane, which are readily available either through synthesis or isolation from petroleum. Having a relatively high vapor pressure at CVD diamond growth temperatures, these could then be put into a CVD chamber in the vapor phase to act as nucleation sites for diamond growth. By adjusting the conditions appropriately (time, temperature, gas composition including hydrogen and carbon source) tetramantanes, pentamantanes, hexamantanes, etc. can be grown in the gas phase. As the diamondoids grow larger, they precipitate from the vapor as their vapor pressure decreased. A cooler, collector substrate collects these larger diamondoids. If still larger diamondoids are desired, heating or mechanical agitation of the collector substrate keeps the diamondoids in the growth environment as long as desired. By this means, larger diamondoids/diamonds, e.g. diamondoids with ca. 100 carbons which could be used for photonic crystals and for catalysts will form. Furthermore, by beginning with a derivitized diamondoid, e.g., derivitized with an amine or borane group, one can effectively dope the larger diamondoids being grown with nitrogen or boron. Alternatively, one can derivitize and/or dope the diamondoid with functional groups by addition of appropriate reactants in the CVD chamber.

CVD growth of diamonds is believed to occur on a heated substrate via hydrogen extraction and hydrogen and carbon containing radical attachment mechanisms. Diamondoids with a sufficient number of internal degrees of freedom should act in the same way as the small diamond seed crystals used to nucleate conventional CVD diamond growth. A detailed description of this process can be found in the book *Physics and Applications of CVD Diamond*, Satoshi Koizumi; Christoph Nebel, Milos Nesladek, John Wiley and Sons, 2008.

Figure 7:
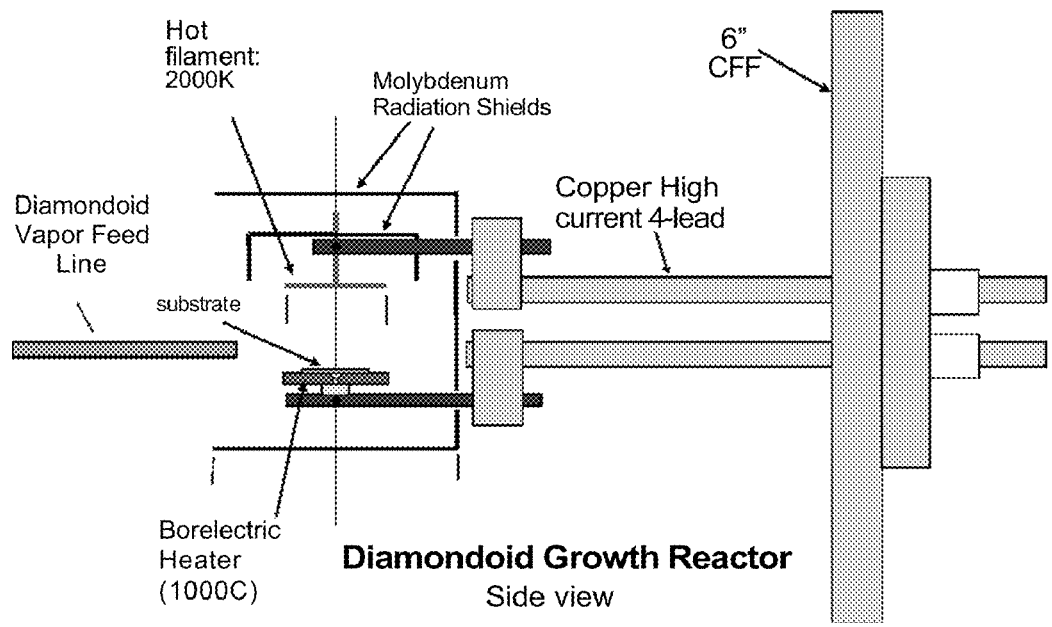
FIG. 7 illustrates a side-view of a diamond growth reactor for producing higher diamondoids by a CVD process.
Figure 8:
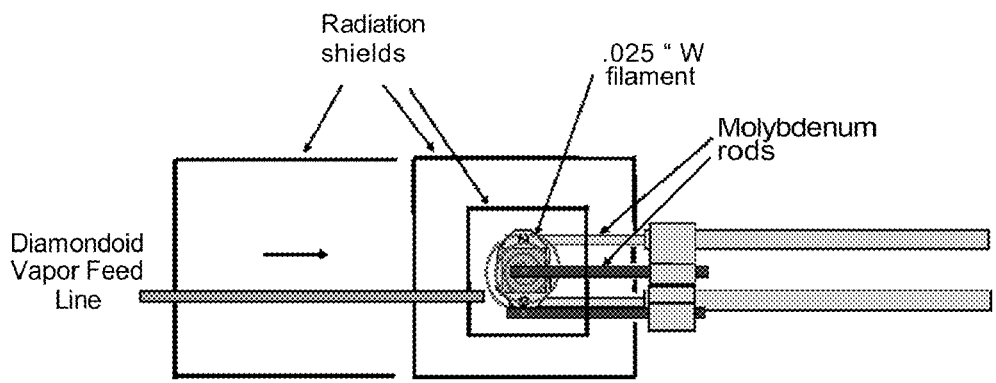
FIG. 8 illustrates a plan-view of a diamond growth reactor for producing higher diamondoids by a CVD process.
Figure 9:
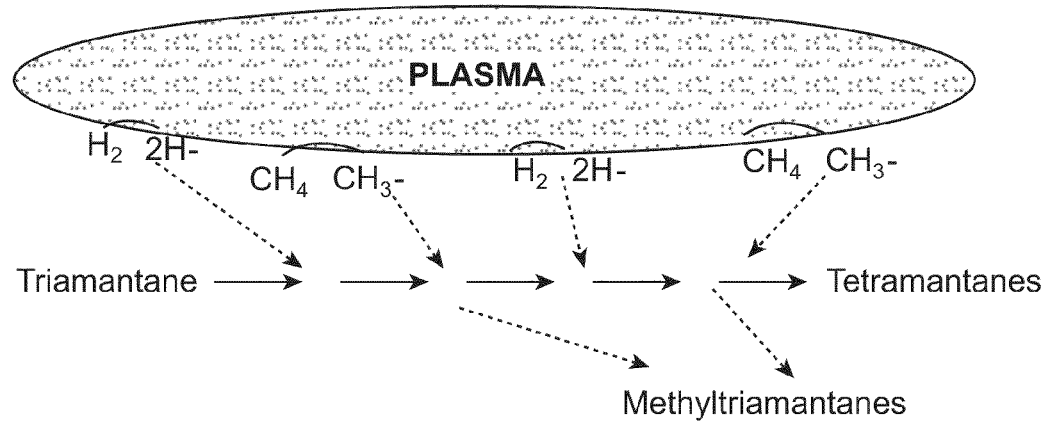
FIG. 9 represents a CVD free-radical reaction sequence in which higher diamondoids are formed from lower ones in addition to intermediate methylated precursors.
Figure 10:
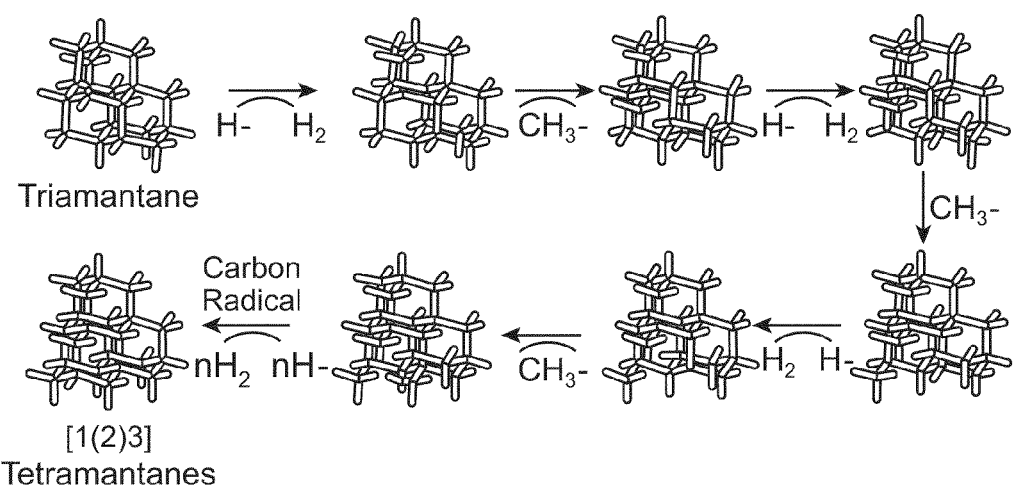
FIG. 10 illustrates CVD reaction steps in which sequential diamondoid radical formation/radical quenching with CVD-generated methyl radicals leads to formation of the next higher diamondoid species.

A modification of a traditional hot-filament reactor designed for growing higher diamondoids is shown in FIGS. 7 and 8. A vacuum chamber maintained at a pressure of approximately 1 Torr is filled with hydrogen (ca. 99%) and a carbon containing gas (e.g., $CH_4$ ca. 1%). The filament is heated to approximately 2000K to dissociate the hydrogen, thereby providing a source of atomic hydrogen. The diamondoid gas is supplied by a tube through the radiation shields. The collector substrate is placed within the radiation shield, and maintained at a temperature too low to produce diamond growth reactions. The temperature gradient between the filament and the collector substrate provides a range of conditions suitable to cause growth on the diamondoid surfaces. Growth rate and efficiency can be optimized by changing geometry and gas composition in the reactor. Formation of diamondoids of increasing diamond crystal-cage count by this CVD system is illustrated in FIGS. 9 and 10. Hydrogen radicals (atoms) generated from hydrogen gas in the CVD chamber strip hydrogen atoms from diamondoid seed molecules, generating diamondoid free radicals that add carbon atoms by quenching with methyl radicals formed from methane in the CVD plasma. Methylated diamondoids are major products leading to subsequent ring/cage closure and formation of the next higher diamondoid with a cage count of N+1, where N is the number of diamond crystal cages in the seed diamondoid. FIG. 10 shows an example reaction sequence in the formation of [1(2)3]tetramantane from triamantane in the CVD chamber. Hydrogen atoms are stripped from a seed diamondoid face giving rise to a radical that is quenched by a methyl radical producing a methylated intermediate. Sequential 1, 3, 6 addition of methyl radicals by this mechanism generates the corresponding trimethyltrimantane in which the [1(2)3]tetramantane is formed by carbon radical addition, hydrogen abstraction, and ring/cage closure. This sequence can also form pentamantanes from tetramantanes, hexamantanes from pentamantanes, heptamantanes from hexamantanes, and so on.

All patents and publications referenced herein are hereby incorporated by reference to an extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A method for synthesizing higher diamondoid molecules, the method comprising
    providing sufficient energy to a reactant precursor composition comprising diamondoid molecules having at least 3 cages so as to create free radical species,
    allowing a reaction to occur between the free radical species and the diamondoid molecules having at least 3 cages to thereby add at least one cage to the molecules and yield augmented higher diamondoid species, and
    recovering the augmented higher diamondoid species.
2. The method of claim 1, wherein the energy is provided in a reactor.
3. The method of claim 2, wherein the reactor is under an inert atmosphere.
4. The method of claim 1, wherein the free radicals are provided in association with a plasma.
5. The method of claim 1, wherein the reaction occurs in a gaseous phase and the augmented higher diamondoid species condense on a substrate.
6. The method of claim 1, wherein the reaction takes place at a temperature of between 200° C. and 500° C.
7. The method of claim 1, wherein the reaction takes place in the presence of a catalyst.
8. The method of claim 7, wherein the catalyst comprises a super-acid.
9. The method of claim 7, wherein the catalyst comprises montmorillonite.
10. The method of claim 1, wherein the reactant precursor composition comprises a quantity of at least one non-diamondoid reactant species.
11. The method of claim 10, wherein the at least one non-diamondoid reactant species comprises isobutane or isobutene.
12. The method of claim 1, wherein the reactant precursor composition comprises a quantity of lower diamondoid species selected from the group consisting of adamantane, diamantane, and combinations thereof.
13. The method of claim 1, wherein providing sufficient energy to the reactant precursor composition so as to create free radical species and allowing a reaction to occur between the free radical species and the diamondoid molecules is arrived at via:
    a) seeding a substrate with a diamondoid molecule; and
    b) growing a diamondoid film on said substrate in a CVD chamber, via chemical vapor deposition, wherein the diamondoid molecules serve as nucleating seeds for growth of said diamondoid film.
14. The method of claim 13, wherein the CVD chamber contains a substrate operable for condensing larger diamondoids from the gas phase.
15. The method of claim 14, wherein the substrate is agitated so that condensed diamondoids are re-introduced into a diamondoid growth environment.
16. The method of claim 14, wherein the substrate temperature is controlled to condense diamondoids of desired size.
17. A method for synthesizing higher diamondoid molecules, the method comprising:
    providing a reactant precursor composition comprising diamondoid molecules having at least 3 cages,
    imparting energy to the reactant precursor composition so as to effect augmentation of the diamondoid molecules having at least 3 cages so as to thereby add at least one cage to said molecules, and so as to thereby provide a higher diamondoid composition comprising augmented higher diamondoids, and
    recovering the augmented higher diamondoids from the higher diamondoid composition.
18. The method of claim 17, wherein the reactant precursor composition comprising diamondoid molecules having at least 3 cages comprises diamondoid species that have been extracted from a petroleum resource.

* * * * *